(12) United States Patent
Hengstenberg et al.

(10) Patent No.: US 8,342,178 B2
(45) Date of Patent: Jan. 1, 2013

(54) DEVICE FOR TAKING AND ANALYZING BREATHING GAS SAMPLES

(75) Inventors: Andreas Hengstenberg, Reinfeld (DE); Stefan Zimmermann, Reinfeld (DE)

(73) Assignee: Dräger Medical GmbH, Lübeck (DE)

( * ) Notice: Subject to any disclaimer, the term of this patent is extended or adjusted under 35 U.S.C. 154(b) by 968 days.

(21) Appl. No.: 12/396,034

(22) Filed: Mar. 2, 2009

(65) Prior Publication Data

US 2009/0281443 A1 Nov. 12, 2009

(30) Foreign Application Priority Data

May 8, 2008 (DE) .......................... 10 2008 022 761

(51) Int. Cl.
*F16K 31/02* (2006.01)
(52) U.S. Cl. .......... 128/204.21; 128/204.22; 128/204.23
(58) Field of Classification Search ............ 128/204.21–204.23, 205.24, 205.27
See application file for complete search history.

(56) References Cited

U.S. PATENT DOCUMENTS

| | | | | |
|---|---|---|---|---|
| 4,619,269 A | * | 10/1986 | Cutler et al. .................. | 600/532 |
| 5,069,220 A | * | 12/1991 | Casparie et al. .............. | 600/532 |
| 5,111,827 A | * | 5/1992 | Rantala .......................... | 600/532 |
| 5,293,875 A | * | 3/1994 | Stone ............................. | 600/532 |
| 5,531,096 A | * | 7/1996 | Castor ............................ | 73/23.2 |
| 5,873,361 A | * | 2/1999 | Hakala ....................... | 128/204.23 |
| 6,520,180 B1 | * | 2/2003 | Sahmkow et al. ........ | 128/204.21 |
| 7,290,544 B1 | * | 11/2007 | Sarela et al. ............. | 128/202.22 |
| 2005/0022811 A1 | * | 2/2005 | Kiesele et al. ........... | 128/203.12 |

FOREIGN PATENT DOCUMENTS

| | | |
|---|---|---|
| DE | 1 203 021 B | 10/1965 |
| DE | 196 19 763 A1 | 11/1997 |
| DE | 19619763 A1 * | 11/1997 |
| DE | 101 58 288 A1 | 5/2003 |
| DE | 10 2006 039 140 A1 | 3/2008 |

* cited by examiner

*Primary Examiner* — Oren Ginsberg
(74) *Attorney, Agent, or Firm* — McGlew and Tuttle, P.C.

(57) ABSTRACT

A device provided for taking and continuously analyzing and monitoring breathing gas samples from defined, current phases of breathing of a patient is equipped with a breathing gas line (1) and with a sensor (2) for recognizing the current phases of breathing. A sampling line (3) is provided from the breathing gas line (1). The sampling line (3) is connected to a first gas delivery device (44) via a sample gas loop (4); with a measuring line (8) from the sampling line (3) to a sensor system (6) with a second gas delivery device (66) for the analysis of breathing gas samples; with a valve (5) in the sampling line (3) for controlling the breathing gas sample flow from defined, current phases of breathing into the sensor system (6) and into the sample gas loop (4), and with a control unit (7), which is connected at least to the gas delivery device (44) and to the valve (5), so that a continuous volume flow of breathing gas samples can be fed to the sensor system (6) from the defined, current phases of breathing.

23 Claims, 2 Drawing Sheets

DEVICE FOR TAKING AND ANALYZING BREATHING GAS SAMPLES

CROSS REFERENCE TO RELATED APPLICATIONS

This application claims the benefit of priority under 35 U.S.C. §119 of German Patent Application DE 10 2008 022 761.7 filed May 8, 2008, the entire contents of which are incorporated herein by reference.

FIELD OF THE INVENTION

The present invention pertains to a device for taking and analyzing breathing gas samples.

BACKGROUND OF THE INVENTION

Such a device for taking inspiratory and/or expiratory, i.e., defined breathing gas samples, which belong to a defined phase of breathing, from the breathing gas of a patient for analyzing substances contained in the breathing gas samples is disclosed in DE 196 19 763 A1, where certain breathing gas samples from the phase of inspiration and/or expiration are enriched by a reversing valve, but no provisions are made for the continuous measurement of defined breathing gas samples only from breaths following each other in time.

The analysis of or determination of concentrations in breathing gas samples in such a way that the analysis or determination is resolved for individual breaths makes it possible to determine and monitor the status of a patient, for example, based on the expired concentrations or quantities of a characteristic active ingredient such as propofol and/or metabolites thereof or of substances formed endogenously, for example, acetone, which can be found in the expired air.

When analyzing breathing gas samples of patients who are respirated mechanically (also known as ventilated) or are not able to cooperate by means of sensors or other measuring devices, the response times of the measuring means used must be coordinated with the respiration rate in order to make possible informative measurements during the phase of inspiration and/or the phase of expiration. The response times of many measuring systems do not meet these requirements concerning the determination of the concentrations in such a way that the determination is resolved for individual breaths, so that these measuring systems can be used for breathing gas analysis to a limited extent only.

Exact assignment of the measurement results obtained to defined phases of breathing, for example, inspiration, expiration, end tidal phase, etc., is very important for the interpretation of measurement results obtained for breathing gas samples, because they provide information on the origin of the measured substances or metabolites, for example, from the room air, from the upper airways or from the alveoli.

SUMMARY OF THE INVENTION

An object of the present invention is to provide a device for taking and continuously analyzing and monitoring breathing gas from defined, current phases of breathing for measuring systems, whose time resolution is not sufficient for the measurement of substances within individual phases of breathing.

According to the invention, a device is provided for taking and analyzing breathing gas samples. The device includes a breathing gas line, a sensor operatively connected to the breathing gas line for recognizing the current phases of breathing, a first gas delivery device, a sample gas loop and a sampling line for sampling from the breathing gas line. The sampling line is connected via the sample gas loop to the first gas delivery device. A sensor system is provided with a second gas delivery device with the second gas delivery device for the analysis of breathing gas samples. A measuring line is provided from the sampling line to the sensor system. A valve is provided in the sampling line for controlling breathing gas sample flow from defined current phases of breathing into the sensor system and into the sample gas loop. A control unit is connected at least to the sensor for recognizing current phases of breathing, to the first gas delivery device and to the valve so that a continuous volume flow of breathing gas samples can be fed to the sensor system from the defined current phases of breathing.

Using the device described, the breathing gas volume of the breathing gas samples taken intermittently from the main stream is advantageously delivered into the side stream into a sample gas loop. Using the arrangement described, the sample gas flow taken intermittently can be transformed in the side stream into a continuous sample gas flow. The continuous sample gas flow is fed to the associated sensor system for the analysis or measurement.

Other advantageous embodiments and variants of the device may be provided.

For example, it is thus advantageously possible to condition, especially to temper, or to filter the breathing gas samples to be measured by means of corresponding means in the sample gas loop and to bring them into line concerning their moisture content.

For example, the moisture content in a breathing gas sample can be changed by a Nafion tube. The water content in the breathing gas sample is thus usually reduced in order to avoid condensation in the device. Condensation can also be avoided by tempering the gas-carrying system at approximately 40° C. A replaceable bacteria filter may also be provided at the inlet for hygienic reasons.

The materials or elements of the device, which come into contact with the breathing gas or with the breathing gas sample, must be as inert as possible, i.e., they must not interact with the substances to be analyzed in the breathing gas samples, in order to avoid a possible distortion of measurement results. Tubes made of TEFLON (polytetrafluoroethene—PTFE) or PFA (perfluoroalkoxy polymers) have proved to be suitable for this.

Mixing of breathing gas samples, which are taken at different points in time, and mixing of breathing gas samples in the sample gas loop with ventilating gas, i.e., usually room air, can be minimized by a defined selection of the internal diameters of the tube material used for the sample gas loop. Tubes with an internal diameter in the range of about 1 mm to 3 mm have proved to be suitable.

An exemplary embodiment of a device for taking and analyzing breathing gas samples will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
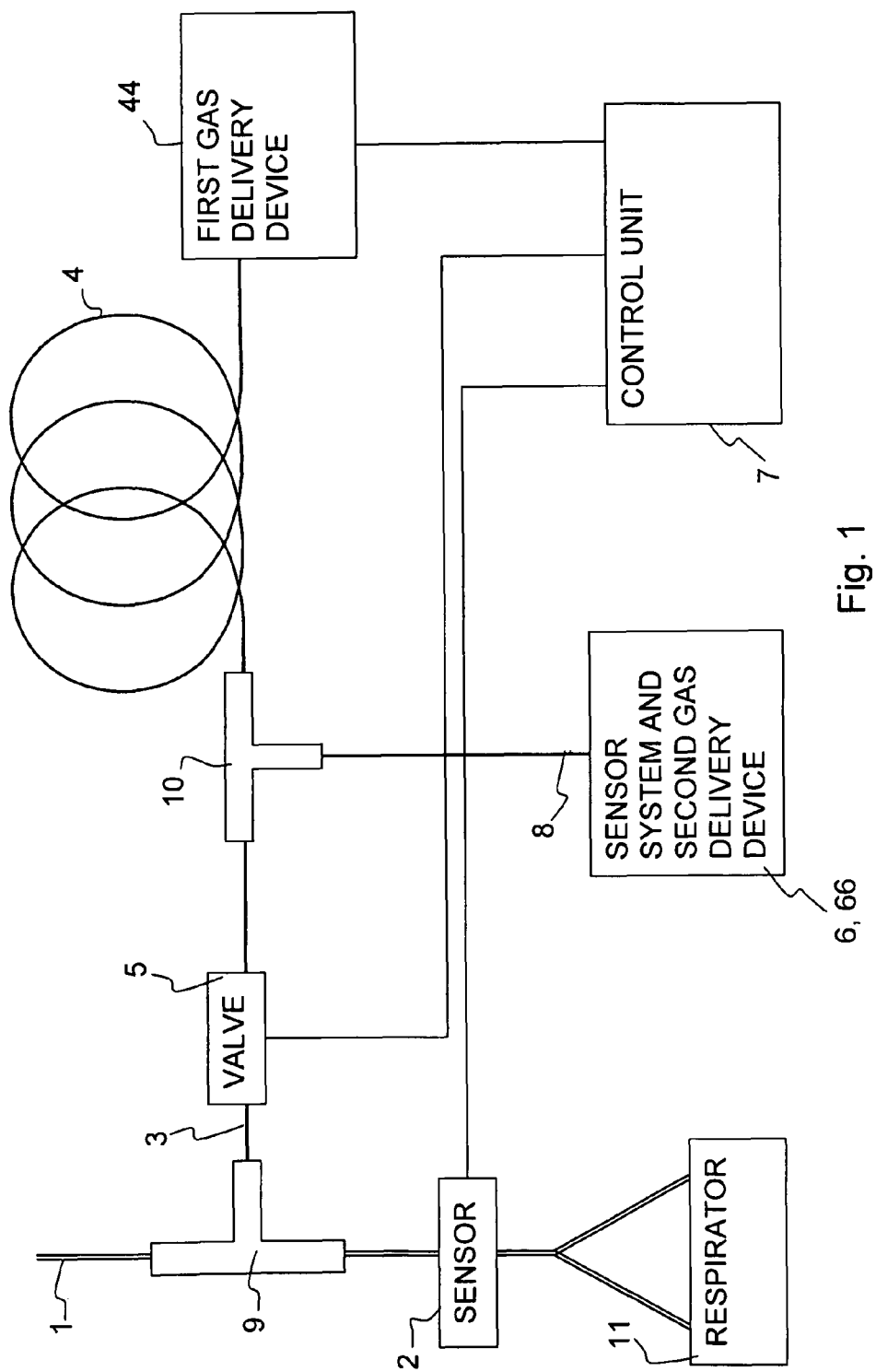
FIG. 1 is a schematic design of a device for taking and analyzing breathing gas samples.

Referring to the drawings in particular, a patient respirated mechanically by means of a respirator 11 is connected to a breathing gas line 1.

The particular current phase of breathing, i.e., for example, expiration or end-tidal expiration, is determined by means of a sensor 2 in or at the breathing gas line 1, for example, on the basis of the $CO_2$ content, which depends on the patient's phase of breathing and is determined, for example, by means of an infrared sensor or generally a sensor.

If the $CO_2$ concentration in the breathing air exceeds a defined value, valve 5 is opened by the control unit 7 and end-tidal breathing gas directly reaches the sensor system 6 as well as the sample gas loop 4 by the activation, via control unit 7, of a first gas delivery device 44, with which breathing gas is delivered via the first T-piece 9 and the second T-piece 10 after actuation of valve 5 into both the sensor system 6 with a second gas delivery device 66 and the sample gas loop 4.

When the $CO_2$ concentration in the breathing gas drops below a predefined value, valve 5 is closed during the phase of inspiration. With valve 5 closed, end-tidal breathing air now reaches the sensor system 6 from the sample gas loop 4 via the second T-piece 10. The sample gas loop 4 is ventilated beginning from the first gas delivery device 44. This can be carried out, for example, by an additional valve at the outlet of the sample gas loop 4 or by the gas delivery device 44 being designed in the form of a pump, which guarantees sufficient ventilation, for example, in the form of a gas delivery device 44 designed as a blade type pump, when stopped.

A corresponding ventilating valve is provided between the gas delivery device 44 and the sample gas loop 4 in case of other pumps, for example, diaphragm pumps, which do not permit direct ventilation of the sample gas loop 4.

The sample gas loop 4 made of a tube-like plastic may have a volume of 50 mL to 400 mL in practical use.

At a hypothetical respiration rate of 12 breaths per minute, 7 mL to 10 mL of end-tidal breathing gas is taken via the sampling line 3, so that breathing gas reaches the sensor system 6 and the sample gas loop 4 intermittently via the second T-piece 10. On average, 84 mL to 120 mL per minute is sent from the patient's expired flow into the device. For example, 70 mL per minute is sent continuously to the sensor system 6 through the second T-piece 10. Uninterrupted admission of or supply with end-tidal expired air is thus guaranteed for sensor system 6.

If valve 5 remains closed for a long time, so that the sample gas loop 4 is not filled any more, a warning is sent, for example, via the control unit 7 and/or the measured values are no longer taken into account or are marked as invalid.

The flow rates and volumes taken of the breathing gas samples can be monitored by volume flow sensors (flow sensors) which are known per se and are not shown in FIG. 1 and/or they may be preset by a corresponding design of the gas delivery means 44, 66 or by the gas delivery rates set on the gas delivery devices 44, 66.

A volume flow sensor/flow sensor is preferably arranged between the sample gas loop 4 and the gas delivery device 44 with an optional ventilating valve. Both the flow and the volume of the breathing gas taken, which enters the sample gas loop 4, and the flow and volume of the ventilating gas can be monitored with this.

Especially electrochemical sensors, infrared sensors, semiconductor sensors, mass spectrometers (MS), ion mobility spectrometers (IMS), and SAW (Surface Acoustic Wave) sensors may be used in the sensor system 6. The sensor system 6 may also have a special inlet system, for example, a diaphragm inlet and/or a gas-conditioning system or gas-drying system via a Nafion tube.

Figure 2:
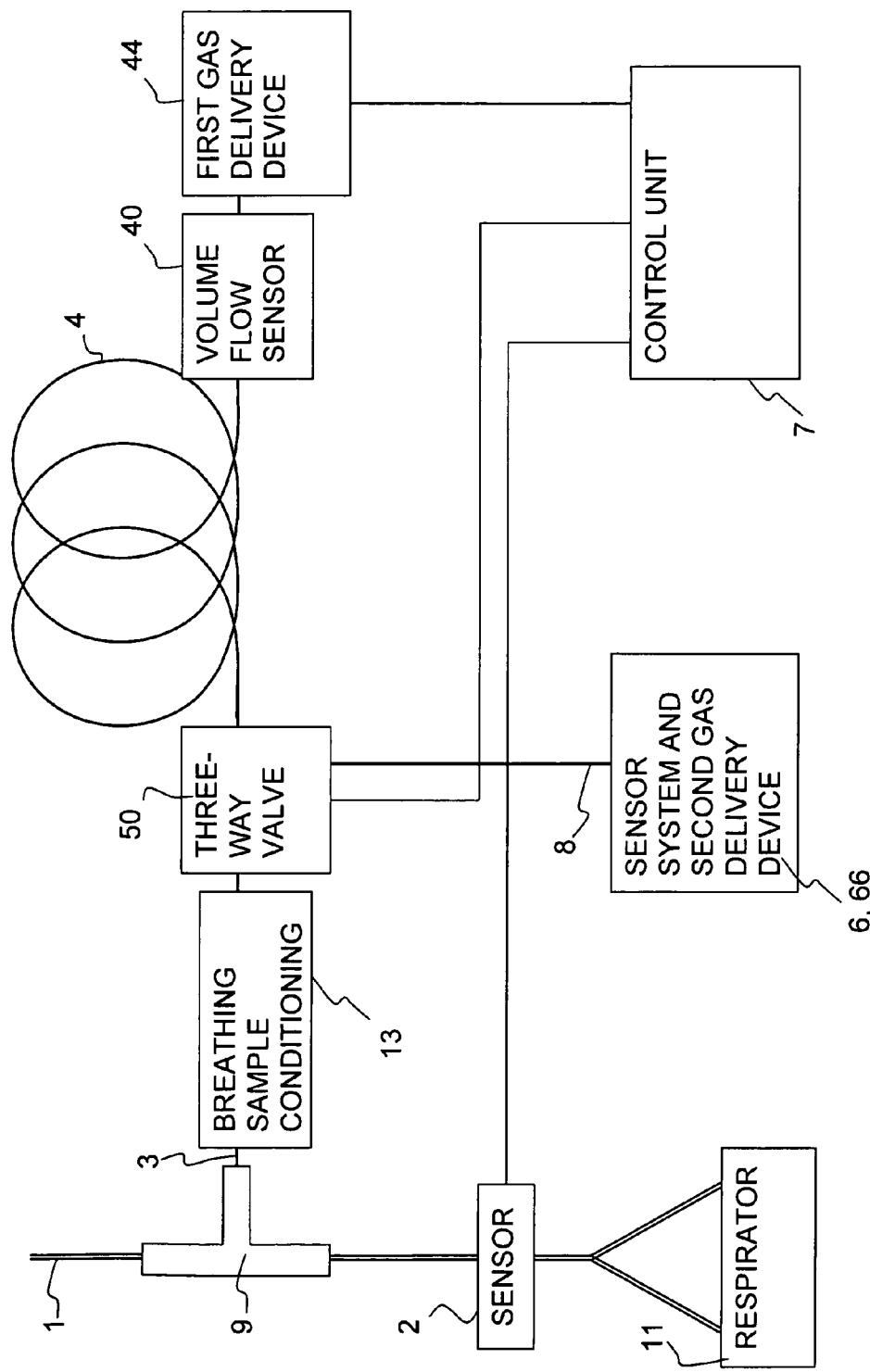
FIG. 2 is a schematic design of a device for taking and analyzing breathing gas samples showing design variants.

The device comprising the elements valve 5 and T-piece 10 may also be embodied in the form of a three-way valve, such as a single assembly unit three-way valve 50 as shown in FIG. 2.

As shown in FIG. 2, a breathing sample conditioning means 13 may be provided for conditioning the breathing gas samples taken. The conditioning means 13 may comprise at least one of a heat tempering element, gas-drying elements, a heating device, a water trap and a dehumidifying tube. The water trap and other features of the conditioning means may be arranged at the sample gas inlet in the sampling line 3 in front of valve 5. To avoid condensation, the entire device may also be heated by means of a heater as a conditioning means 13.

As shown in FIG. 2, a volume flow sensor 40 may be provided in the sample gas loop for detecting volume flows or gas volume flows exchanged in the sample gas loop.

Control unit 7 also comprises the option of a combined measuring and control unit for the device.

Device elements in the singular form also comprise the plural form and vice versa.

While specific embodiments of the invention have been shown and described in detail to illustrate the application of the principles of the invention, it will be understood that the invention may be embodied otherwise without departing from such principles.

What is claimed is:

1. A device for taking and analyzing breathing gas samples, the device comprising:
    a breathing gas line;
    a sensor operatively connected to said breathing gas line for recognizing the current phases of breathing;
    a first gas delivery device;
    a sample gas loop;
    a sampling line for sampling from said breathing gas line, wherein said sampling line is connected via said sample gas loop to said first gas delivery device;
    a sensor system with a second gas delivery device, said sensor system for the analysis of breathing gas samples;
    a measuring line from said sampling line to said sensor system;
    a valve in said sampling line for controlling breathing gas sample flow from defined current phases of breathing into said sensor system and into said sample gas loop, said valve comprising an open position and a closed position, said sample loop being in communication with said first gas delivery device, said sensor system with said second delivery device and at least a portion of said measuring line with said valve in said open position and said closed position; and
    a control unit connected at least to said sensor for recognizing current phases of breathing, to said first gas delivery device and to said valve so that a continuous volume flow of breathing gas samples can be fed to the sensor system from the defined current phases of breathing.

2. A device in accordance with claim 1, further comprising a respirator wherein said breathing gas line is connected to said respirator for the mechanical respiration of a patient, said sensor detecting a carbon dioxide level in said breathing gas sample flow in said breathing gas line, said control unit controlling said valve such that said valve is in said open position when said carbon dioxide level is greater than a predetermined value and such that said valve is in said closed position when said carbon dioxide level is less than said predetermined value, said sample gas loop having one or more helical portions, said one or more helical portions being connected to said first gas delivery device.

3. A device in accordance with claim 1, wherein the sample gas loop has a helical or tubular design and has a volume of 50 mL to 400 mL.

4. A device in accordance with claim 1, wherein said valve and a T-piece comprise one assembly unit.

5. A device in accordance with claim 4, wherein said one assembly unit is a three-way valve.

6. A device in accordance with claim 1, wherein at least one of said sensor and said sensor system have an electrochemical sensor, a semiconductor or an infrared sensor.

7. A device in accordance with claim 1, wherein at least one of said sensor and said sensor system have a mass spectrometer, an ion mobility spectrometer (IMS), and a surface acoustic wave (SAW) sensor.

8. A device in accordance with claim 1, wherein the defined current phases of breathing are expiration phases including at least end-tidal expiration phases.

9. A device in accordance with claim 1, wherein the device is part of a respirator and comprises an assembly unit with said respirator.

10. A device in accordance with claim 1, wherein the device or parts of the device is/are equipped with conditioning means for the breathing gas samples taken, said conditioning means comprising at least one of a tempering element, gas-drying elements, a heating device, a water trap and a dehumidifying tube.

11. A device in accordance with claim 2, wherein said sample gas loop is formed by one or more tube systems, said first gas delivery device being actuated via said control unit when said valve in said open position such that at least said sample loop receives said breathing gas sample flow, said sensor system receiving said breathing gas sample flow with said valve in said open position, wherein at least a portion of said breathing gas sample flow in said sample loop is delivered to said sensor system with said valve in said closed position, wherein a patient receives breathing gas via said breathing gas line with said valve in said closed position.

12. A device in accordance with claim 1, further comprising a volume flow sensor in the sample gas loop for detecting volume flows or gas volume flows exchanged in said sample gas loop.

13. A device for taking and analyzing breathing gas samples, the device comprising:
a breathing gas line;
a first gas delivery device;
a sensor system with a second gas delivery device with said sensor system for the analysis of breathing gas samples;
a sensor operatively connected to said breathing gas line for recognizing the current phases of breathing;
a first T-piece with branches connected to said breathing gas line;
a sampling line connected to said breathing gas line via another branch of said first T-piece;
a second T-piece with branches connected to said sampling line;
a sample gas loop connected between said sampling line and said first gas delivery device;
a measuring line connected to another branch of said second T-piece and connected to said sensor system;
a valve in said sampling line for controlling breathing gas sample flow into said sampling line, said valve being arranged between said first T-piece and said sample loop; and
a control unit connected at least to said sensor for recognizing current phases of breathing, to said first gas delivery device and to said valve so that breathing gas samples can be fed to the sampling line, said sample gas loop, said measuring line and said sensor system based on recognized current phases of breathing.

14. A device in accordance with claim 13, further comprising a respirator wherein the breathing gas line is connected to said respirator for the mechanical respiration of a patient, said valve being arranged between said first T-piece and said second T-piece, said second T-piece being arranged between said sample loop and said valve, said second T-piece being adjacent to said sample loop, said valve comprising an open position and a closed position, said sample loop being in communication with said first gas delivery device, said sensor system with said second delivery device and at least a portion of said measuring line with said valve in said open position and said closed position, said gas sample loop comprising at least one portion having a helical contour, said at least one portion being in communication with said first gas delivery device.

15. A device in accordance with claim 13, wherein the sample gas loop has a helical or tubular design and has a volume of 50 mL to 400 mL.

16. A device in accordance with claim 13, wherein said valve and said second T-piece comprise one assembly unit with said valve comprising a three-way valve.

17. A device in accordance with claim 14, wherein said control unit receives signals from said sensor for recognizing expiration phases including at least end-tidal expiration phases, said sample loop being in communication with said first gas delivery device and said second gas delivery device with said valve in said open position and said closed position, said sensor detecting a carbon dioxide level in a breathing gas sample flow in said breathing gas line, said control unit controlling said valve such that said valve is in said open position when said carbon dioxide level is greater than a predetermined value and said valve is in said closed position when said carbon dioxide level is less than said predetermined value.

18. A device in accordance with claim 14, wherein the device is connected as a part of said respirator and comprises an assembly unit with said respirator.

19. A device in accordance with claim 14, further comprising breathing sample conditioning means for conditioning the breathing gas samples taken, said conditioning means comprising at least one of a heat tempering element, gas-drying elements, a heating device, a water trap and a dehumidifying tube, said breathing gas line, said first T-piece, said sample line, said valve, said second T-piece, said sample loop, said first gas delivery device, said measuring line and said sensor system defining a first sample gas flow path with said valve in said open position, at least said second T-piece, said sample loop and said portion of said measuring line defining a second sample gas flow path with said valve in said closed position, wherein said sample breathing gas flow is delivered to said sensor system via said second sample gas flow path with said valve in said closed position, wherein a patient receives breathing gas via said breathing gas line with said valve in said closed position.

20. A device in accordance with claim 13, further comprising a volume flow sensor in the sample gas loop for detecting volume flows or gas volume flows exchanged in said sample gas loop.

21. A device in accordance with claim 13, wherein at least one of said sensor and said sensor system have an electrochemical sensor, a semiconductor or an infrared sensor.

22. A device in accordance with claim 13, wherein at least one of said sensor and said sensor system have a mass spectrometer, an ion mobility spectrometer (IMS), and a surface acoustic wave (SAW) sensor.

23. A device in accordance with claim 13, wherein said sample gas loop is formed by one or more tube systems.

* * * * *